United States Patent
Fujita et al.

(10) Patent No.: US 10,626,281 B2
(45) Date of Patent: Apr. 21, 2020

(54) INK JET INK COMPOSITION

(71) Applicant: Seiko Epson Corporation, Tokyo (JP)

(72) Inventors: Tomohiro Fujita, Chino (JP); Chikako Fujita, Chino (JP); Kana Ozaki, Chino (JP); Yoshifumi Ito, Matsumoto (JP)

(73) Assignee: Seiko Epson Corporation (JP)

( * ) Notice: Subject to any disclaimer, the term of this patent is extended or adjusted under 35 U.S.C. 154(b) by 304 days.

(21) Appl. No.: 15/714,075

(22) Filed: Sep. 25, 2017

(65) Prior Publication Data

US 2018/0094153 A1 Apr. 5, 2018

(30) Foreign Application Priority Data

Sep. 30, 2016 (JP) ................... 2016-194422
Jun. 7, 2017 (JP) ................... 2017-112297

(51) Int. Cl.
| | | |
|---|---|---|
| C09D 11/328 | (2014.01) |
| C09D 11/40 | (2014.01) |
| C09B 3/60 | (2006.01) |
| C09B 67/00 | (2006.01) |
| C07C 317/14 | (2006.01) |
| C09B 67/46 | (2006.01) |
| C09D 11/38 | (2014.01) |

(52) U.S. Cl.
CPC .......... C09D 11/328 (2013.01); C07C 317/14 (2013.01); C09B 3/60 (2013.01); C09B 67/0084 (2013.01); C09D 11/38 (2013.01); C09D 11/40 (2013.01)

(58) Field of Classification Search
None
See application file for complete search history.

(56) References Cited

U.S. PATENT DOCUMENTS

| | | | | |
|---|---|---|---|---|
| 5,169,436 | A * | 12/1992 | Matrick | C09D 11/30 106/31.58 |
| 5,300,143 | A * | 4/1994 | Schwarz, Jr. | C09D 11/30 106/31.43 |
| 5,540,764 | A * | 7/1996 | Haruta | C09D 11/30 106/31.58 |
| 5,782,967 | A * | 7/1998 | Shirota | C09D 11/38 106/31.58 |
| 7,416,591 | B2 * | 8/2008 | Grund | C09B 67/0034 106/31.43 |
| 8,053,494 | B2 * | 11/2011 | Stovold | B41M 3/005 523/160 |
| 8,534,821 | B2 * | 9/2013 | Kawashima | C09D 11/322 347/100 |
| 8,764,178 | B2 * | 7/2014 | Tamanuki | B41J 2/165 347/100 |
| 8,871,014 | B2 * | 10/2014 | Kim | C09D 11/52 106/31.61 |
| 2013/0284062 | A1 | 10/2013 | Morimitsu et al. | |
| 2013/0333591 | A1 * | 12/2013 | Vanbesien | C09D 11/102 106/31.49 |
| 2017/0183525 | A1 * | 6/2017 | Fujioka | B41J 2/17503 |
| 2017/0183527 | A1 * | 6/2017 | Kojima | B41J 2/01 |
| 2018/0273763 | A1 * | 9/2018 | Ito | C09B 67/0089 |

FOREIGN PATENT DOCUMENTS

| | | |
|---|---|---|
| JP | 10-298477 A | 11/1998 |
| JP | 2004-285241 A | 10/2004 |
| JP | 2008-050589 A | 3/2008 |
| JP | 2010-018739 A | 1/2010 |
| JP | 2013-227568 A | 11/2013 |

OTHER PUBLICATIONS

Solvent Blue 101, www.worlddyevariety.com/solvent-dyes/solvent-blue-101.html, no date available; 8 pages.*
Disperse Red 60, www.worlddyevariety.com/disperse-dyes/disperse-red-60.html, no date available; 12 pages.*

* cited by examiner

*Primary Examiner* — Helene Klemanski
(74) *Attorney, Agent, or Firm* — Harness, Dickey & Pierce, P.L.C.

(57) ABSTRACT

An ink jet ink composition contains a disperse dye, and a compound represented by the following formula (1):

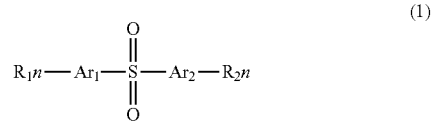

In the formula, $Ar_1$ and $Ar_2$ each independently represent an aryl group; $R_1$ and $R_2$ each independently represent a chemical species selected from the group consisting of hydrogen, alkyl groups having a carbon number of 1 to 3, a sulfo group, $-O-SO_3H$, a carboxy group, and a hydroxy group; and n's each independently represent an integer of 0 to 5.

6 Claims, No Drawings

INK JET INK COMPOSITION

BACKGROUND

1. Technical Field

The present invention relates to an ink jet ink composition.

2. Related Art

Known disperse dye inks contain low-polarity dye fine crystals of several tens of nanometers to less than one micrometer in diameter that is dispersed in an aqueous liquid by using a dispersant and/or a surfactant. A dispersant or a surfactant is essential to keep a disperse dye suspended in a medium (solvent) without settling and thus to control the viscosity and the surface tension to be appropriate as an ink (See, for example, JP-A-10-298477).

Although the disperse dye, which is pulverized into fine crystals before being dispersed, is intrinsically insoluble in water and similar solvents, it has been confirmed that the disperse dye can dissolve at a molecular level in the presence of a solvent, a dispersant, and a surfactant (that is, dissolve in an ink composition). In addition, the saturation solubility of a coloring material in an ink depends on temperature. If the solvent temperature is reduced, the saturation solubility of the coloring material decreases, and the amount of the coloring material corresponding to the temperature difference precipitates out of the ink, accordingly. The composition of ink is changed by evaporation of low-boiling-point components in the vicinity of ink jet nozzles, and the coloring material cannot be kept dispersed or suspended, forming aggregates of foreign matter.

The state of a disperse dye dispersion is easily affected by disturbance and compositional changes in the ink. It is known that, in pale color inks prepared by simply diluting a deep color without changing the proportion of the disperse dye to the dispersant, the state of the dispersion of the disperse dye is not easily maintained. It is desired to minutely adjust the composition of the ink, including the proportion of the dispersant and the disperse dye. Particularly for pale color inks, it has been found that it is not necessarily effective, in maintaining the state of the dispersion of the disperse dye, to add the dispersant with a higher content than the disperse dye, because an excess of the dispersant dissolves the disperse dye and produces foreign matter from the disperse dye, or the portion of the dispersant that has not been involved in dispersing the disperse dye turns into foreign matter.

SUMMARY

An advantage of some aspects of the invention is that it provides an ink jet ink composition in which foreign matter derived components therein is reduced.

The present inventors have conducted intensive research to solve the above issues and found that the issues can be solved by using a specific compound.

According to an aspect of the invention, there is provided an ink jet ink composition containing a disperse dye, and a compound represented by the following formula (1):

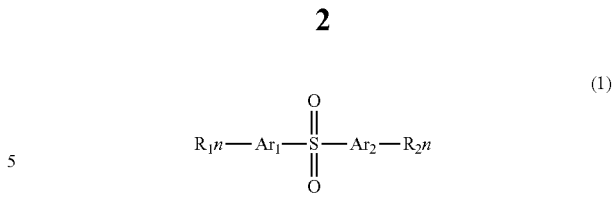

In the formula, $Ar_1$ and $Ar_2$ each independently represent an aryl group; $R_1$ and $R_2$ each independently represent a chemical species selected from the group consisting of hydrogen, alkyl groups having a carbon number of 1 to 3, a sulfo group, —O—SO$_3$H, a carboxy group, and a hydroxy group; and n's each independently represent an integer of 0 to 5. In the ink composition, foreign matter derived from components of the ink is reduced.

Preferably, the proportion of the compound represented by formula (1) in the ink jet ink composition is 0.01 part by mass to 150 parts by mass relative to 1 part by mass of the disperse dye. Preferably, the ink jet ink composition further contains a dispersant. Preferably, the proportion of the total mass of the disperse dye and the compound represented by formula (1) is in the range of 0.24 to 4.0 relative to the mass of the dispersant. Preferably, the proportion of the compound represented by formula (1) is 0.001 part by mass to 1000 parts by mass relative to 1 part by mass of the dispersant. Preferably, the dispersant contains a formalin condensate of an aromatic sulfonic acid compound. Preferably, the molecule of the disperse dye has a condensed ring structure.

DESCRIPTION OF EXEMPLARY EMBODIMENTS

Embodiments of the invention will now be described. However, the invention is not limited to the disclosed embodiments, and various modifications may be made without departing from the scope and spirit of the invention.

Ink Jet Ink Composition

An ink jet ink composition according to an embodiment of the invention contains a disperse dye and a compound represented by the following formula (1):

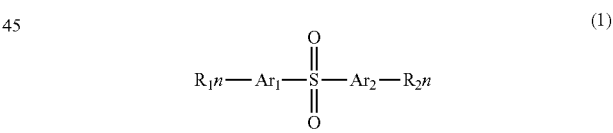

In the formula, $Ar_1$ and $Ar_2$ each independently represent an aryl group; $R_1$ and $R_2$ each independently represent a chemical species selected from the group consisting of hydrogen, alkyl groups having a carbon number of 1 to 3, a sulfo group, —O—SO$_3$H, a carboxy group, and a hydroxy group; and n's each independently represent an integer of 0 to 5.

Known dispersants for disperse dyes include naphthalenesulfonic acid, formalin condensate thereof, and ligninsulfonic acid. These dispersants are, in general, materials having a high molecular weight, produced by sulfonating a fossil fuel compound, such as naphthalene, anthracene, or phenanthrene and further condensing the sulfonated compound with formalin for polynuclearization, or by sulfonating lignin derived from wood or pulp. The coloring material content in pale color inks is lower than that in deep color inks. Accordingly, in the pale color ink, all the dispersant, which is intended to enclose the coloring material, does not necessarily enclose the coloring material, and an excess thereof remains in the liquid. Such an excess dispersant is a cause of foreign matter produced in the ink jet ink composition during storage.

On the other hand, in the present embodiment, a compound that is similar to the disperse dye and represented by formula (1) is added to the ink jet ink composition. This compound acts as an alternative to the disperse dye and is enclosed by the dispersant.

The compound of formula (1) has a sulfonyl bis dimer structure formed by dimerizing one or two aromatic compounds with a sulfonyl group. In this compound, the groups derived from the aromatic compounds are compatible with the disperse dye, while the sulfonyl group is compatible with the dispersant having a highly polar substituent. In general, a disperse dye insoluble in aqueous solvents and a dispersant having a highly polar substituent, such as a sulfo group, so as to disperse the disperse dye have a large difference in polarity. The compound represented by formula (1) can reduce such a polarity difference and increase the affinity or compatibility between the disperse dye and the dispersant.

Consequently, the dispersibility of the disperse dye is increased, and the excess dispersant is reduced. In addition, the compound represented by formula (1) is also satisfactorily dispersed. Thus, the present embodiment reduces occurrence of foreign matter from ink components. The phrase "foreign matter (derived) from ink components" used herein refers to foreign matter derived from the disperse dye, foreign matter derived from the compound represented by formula (1), and foreign matter derived from the dispersant.

Disperse Dye

The ink composition of the present embodiment contains a disperse dye. The disperse dye is a compound suitably used as a dye to color hydrophobic synthetic fiber, such as polyester, nylon, or acetate, and is insoluble or poorly soluble in water.

Disperse dyes are cited as follows.

Yellow disperse dyes include, but are not limited to, C. I. Disperse Yellows 3, 4, 5, 7, 9, 13, 23, 24, 30, 33, 34, 42, 44, 49, 50, 51, 54, 56, 58, 60, 63, 64, 66, 68, 71, 74, 76, 79, 82, 83, 85, 86, 88, 90, 91, 93, 98, 99, 100, 104, 108, 114, 116, 118, 119, 122, 124, 126, 135, 140, 141, 149, 160, 162, 163, 164, 165, 179, 180, 182, 183, 184, 186, 192, 198, 199, 202, 204, 210, 211, 215, 216, 218, 224, 227, 231, and 232.

Orange disperse dyes include, but are not limited to, C. I. Disperse Oranges 1, 3, 5, 7, 11, 13, 17, 20, 21, 25, 29, 30, 31, 32, 33, 37, 38, 42, 43, 44, 45, 46, 47, 48, 49, 50, 53, 54, 55, 56, 57, 58, 59, 61, 66, 71, 73, 76, 78, 80, 89, 90, 91, 93, 96, 97, 119, 127, 130, 139, and 142.

Red disperse dyes include, but are not limited to, C. I. Disperse Reds 1, 4, 5, 7, 11, 12, 13, 15, 17, 27, 43, 44, 50, 52, 53, 54, 55, 56, 58, 59, 60, 65, 72, 73, 74, 75, 76, 78, 81, 82, 86, 88, 90, 91, 92, 93, 96, 103, 105, 106, 107, 108, 110, 111, 113, 117, 118, 121, 122, 126, 127, 128, 131, 132, 134, 135, 137, 143, 145, 146, 151, 152, 153, 154, 157, 159, 164, 167, 169, 177, 179, 181, 183, 184, 185, 188, 189, 190, 191, 192, 200, 201, 202, 203, 205, 206, 207, 210, 221, 224, 225, 227, 229, 239, 240, 257, 258, 277, 278, 279, 281, 288, 298, 302, 303, 310, 311, 312, 320, 324, and 328.

Violet disperse dyes include, but are not limited to, C. I. Disperse Violets 1, 4, 8, 23, 26, 27, 28, 31, 33, 35, 36, 38, 40, 43, 46, 48, 50, 51, 52, 56, 57, 59, 61, 63, 69, and 77.

An example of green disperse dyes may be, but is not limited to, C. I. Disperse Green 9.

Brown disperse dyes include, but are not limited to, C. I. Disperse Brown 1, 2, 4, 9, 13, and 19.

Blue disperse dyes include, but are not limited to, C. I. Disperse Blues 3, 7, 9, 14, 16, 19, 20, 26, 27, 35, 43, 44, 54, 55, 56, 58, 60, 62, 64, 71, 72, 73, 75, 79, 81, 82, 83, 87, 91, 93, 94, 95, 96, 102, 106, 108, 112, 113, 115, 118, 120, 122, 125, 128, 130, 139, 141, 142, 143, 146, 148, 149, 153, 154, 158, 165, 167, 171, 173, 174, 176, 181, 183, 185, 186, 187, 189, 197, 198, 200, 201, 205, 207, 211, 214, 224, 225, 257, 259, 267, 268, 270, 284, 285, 287, 288, 291, 293, 295, 297, 301, 315, 330, and 333.

Black disperse dyes include, but are not limited to, C. I. Disperse Blacks 1, 3, 10, and 24.

Those disperse dyes may be used singly or in combination.

In the present embodiment, disperse dyes having a molecular weight of 380 or less are preferred. The molecular weight of such a disperse dye is preferably 340 or less, more preferably in the range of 270 to 340, and still more preferably in the range of 280 to 340. The use of a disperse dye having a molecular weight of 380 or less increases the transfer efficiency of the ink when used in a sublimation transfer system or the like.

Examples of the disperse dye having a molecular weight of 380 or less include C. I. Disperse Reds 11, 53, 55, 59, 60, and 191; C. I. Disperse Yellows 3, 7, 8, 23, 39, 51, 54, 60, 71, and 163; C. I. Disperse Oranges 1, 20, and 25; C. I. Disperse Blues 19, 26, 56, 72, 81, and 359; and C. I. Disperse Violets 8, 17, 27, and 28. These disperse dyes may be used singly or in combination.

Among these, preferred are C. I. Disperse Reds 60 and 191, C. I. Disperse Blue 359, and other disperse dyes having an anthraquinone skeleton containing a hydrophilic group, such as amino or hydroxy. These dyes tend to be compatible with the compound represented by formula (1).

Preferably, the molecule of the disperse dye has a condensed ring structure of naphthalene, anthracene, phenanthrene, or a derivative thereof. For example, C. I. Disperse Red 60 is represented by the following formula:

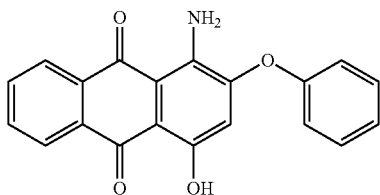 [SMILES: Nc1c(Oc2ccccc2)cc(O)c2c1C(=O)c1ccccc1C2=O]

As shown in this formula, the compound represented by formula (1) is similar to disperse dyes having a condensed ring structure in terms of polarity and molecular structure, and, accordingly, can reduce occurrence of foreign matter from ink components.

The disperse dye content is preferably 0.1% by mass to 12% by mass, more preferably 1% by mass to 10% by mass, and still more preferably 2% by mass to 5% by mass, relative to the total mass of the ink jet ink composition. The term "pale color ink" mentioned herein refers to that having a total disperse dye content of 5% by mass or less. The term "deep color ink" mentioned herein refers to that having a total disperse dye content of more than 5% by mass. The ink jet ink composition of the present embodiment may be a pale color ink or a deep color ink.

Compound Represented by Formula (1)

The compound represented by formula (1) is dispersed in the same manner as the disperse dye by the dispersant without affecting the color of the printed article. The use of such a compound reduces foreign matter resulting from the excess dispersant and increases the affinity or compatibility between the disperse dye and the dispersant, thus improving the stability of the dispersion.

In formula (1), $Ar_1$ and $Ar_2$ each represent an aryl group, and examples thereof include, but are not limited to, phenyl, naphthyl, anthracenyl, and phenanthrenyl. Phenyl, naphthyl, and anthracenyl are advantageous. Preferably, $Ar_1$ and $Ar_2$ are the same aryl group.

$R_1$ and $R_2$ each may represent an alkyl group, and examples of the alkyl group include, but are not limited to, methyl, ethyl, n-propyl, isopropyl, n-butyl, isobutyl, sec-butyl, t-butyl, n-pentyl, neopentyl, n-hexyl, n-heptyl, and n-octyl. Alkyl groups having a carbon number of 1 to 3, particularly, methyl and ethyl, are advantageous.

Examples of the compound represented by formula (1) include (but are not limited to):

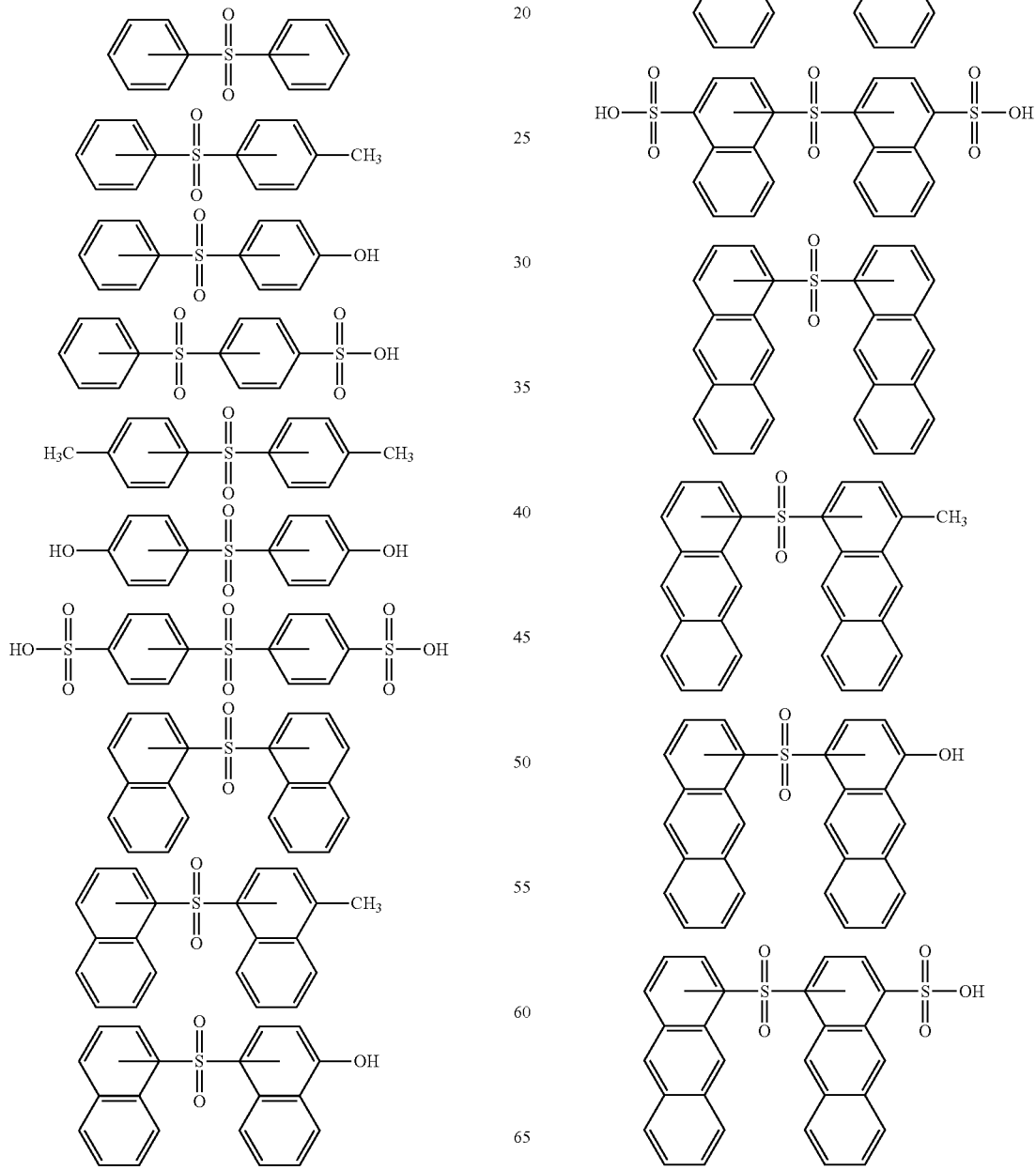

-continued

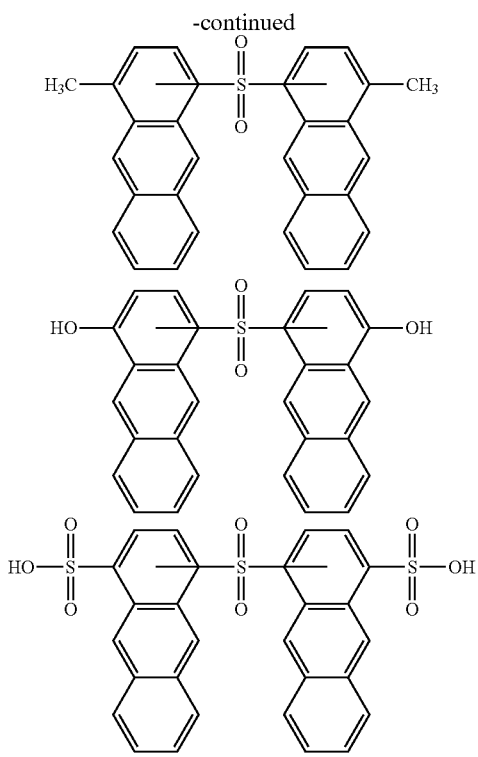

The content of the compound represented by formula (1) is preferably 0.1% by mass to 20% by mass, more preferably 1% by mass to 15% by mass, and still more preferably 2% by mass to 10% by mass, relative to the total mass of the ink jet ink composition. When the content of the compound of formula (1) is 0.1% by mass or more, foreign matter resulting from the excess dispersant tends to decrease, and the affinity or compatibility between the disperse dye and the dispersant tends to increase to improve the stability of the dispersion. When the content of the compound of formula (1) is 20% by mass or less, the compound is likely to be sufficiently dispersed by the dispersant. The compound is thus unlikely to remain undispersed and is therefore unlikely to act as foreign matter.

The proportion of the total content of the disperse dye and the compound of formula (1) to the content of the dispersant, that is, (disperse dye+compound of formula (1))/dispersant), is preferably in the range of 0.24 to 4.0, more preferably in the range of 0.5 to 2.4, and still more preferably in the range of 1.0 to 3.0. When the proportion of these constituents is in such a range, foreign matter resulting from the excess dispersant tends to decrease, and the affinity or compatibility between the disperse dye and the dispersant tends to increase to improve the stability of the dispersion.

The proportion of the compound represented by formula (1) is preferably 0.01 part by mass to 150 parts by mass, more preferably 0.2 part by mass to 5 parts by mass, and still more preferably 0.5 part by mass to 1.5 parts by mass, relative to 1 part by mass of the disperse dye. When the proportion of the compound of formula (1) to the disperse dye is 0.01 part by mass or more, foreign matter resulting from the excess dispersant tends to decrease, and the affinity or compatibility between the disperse dye and the dispersant tends to increase to improve the stability of the dispersion. When the proportion of the compound of formula (1) to the disperse dye is 100 parts by mass or less, the compound is likely to be sufficiently dispersed by the dispersant. The compound is thus unlikely to remain undispersed and is therefore unlikely to act as foreign matter.

The compound of formula (1) may be synthesized by any process without particular limitation, and, for example, by dimerizing one or two aromatic compounds with a sulfonyl group. More specifically, sulfuric acid is added to one or two aromatic compounds that will form the aryl domains of the formula (1) to produce a compound having a sulfonyl bis dimer structure.

Dispersant

The ink jet ink composition of the present embodiment may contain a dispersant. The dispersant may be, but is not limited to, an anionic dispersant, a nonionic dispersant, a polymer dispersant. Anionic dispersants are preferred.

Exemplary anionic dispersants include formalin condensates of alkyl naphthalenesulfonic acids, such as formalin condensate of creosote oil sulfonic acid, formalin condensate of cresol sulfonic acid, formalin condensate of phenolsulfonic acid, formalin condensate of β-naphtholsulfonic acid, formalin condensate of methylnaphthalenesulfonic acid, and formalin condensate of butylnaphthalenesulfonic acid; and formalin condensate of a mixture of β-naphthalenesulfonic acid and β-naphtholsulfonic acid, formalin condensate of a mixture of cresol sulfonic acid and 2-naphthol-6-sulfonic acid, and formalin condensate of ligninsulfonic acid. Formalin condensates of aromatic sulfonic acids are preferred.

Examples of the nonionic dispersant include, but are not limited to, ethylene oxide adducts of phytosterol and ethylene oxide adducts of cholestanol.

Examples of the polymer dispersant include, but are not limited to, partially alkyl-esterified polyacrylic acid, polyalkylene polyamine, polyacrylic acid salts, styrene-acrylic acid copolymer, and vinyl naphthalene-maleic acid copolymer.

The dispersant content is preferably 0.1% by mass to 20% by mass, more preferably 1% by mass to 15% by mass, and still more preferably 2% by mass to 10% by mass, relative to the total mass of the ink jet ink composition. When the dispersant content is 0.1% by mass or more, the disperse dye can be more stably dispersed. When the dispersant content is 20% by mass or less, foreign matter resulting from the excess dispersant tends to decrease.

The proportion of the compound represented by formula (1) is preferably 0.001 part by mass to 1000 parts by mass, more preferably 0.1 part by mass to 5 parts by mass, and still more preferably 0.2 part by mass to 1 part by mass, relative to 1 part by mass of the dispersant. When the proportion of the compound of formula (1) to the dispersant is 0.001 part by mass or more, foreign matter resulting from the excess dispersant tends to decrease, and the affinity or compatibility between the disperse dye and the dispersant tends to increase to improve the stability of the dispersion. When the proportion of the compound of formula (1) to the dispersant is 1000 parts by mass or less, the compound is likely to be sufficiently dispersed by the dispersant. The compound is thus unlikely to remain undispersed and is therefore unlikely to act as foreign matter.

Surfactant

The surfactant may be, but is not limited to, a nonionic, surfactant, a cationic surfactant, or an anionic surfactant. Nonionic surfactants are preferred. By using a nonionic surfactant, ejection stability tends to be improved.

Exemplary nonionic surfactants include, but are not limited to, acetylene glycol-based surfactants, silicone surfactants, polyoxyethylene alkyl ether-based surfactants, polyoxypropylene alkyl ether-based surfactants, polycyclic phenyl ether-based surfactants, sorbitan derivatives, and fluorosurfactants. Among these, acetylene glycol-based surfactants, silicone surfactants, and fluorosurfactants are preferred. Silicone surfactants are more preferred.

Acetylene glycol-based surfactants are superior to the other nonionic surfactants in terms of the ability of appropriately controlling the surface tension and the interface tension, and have the nature of hardly foaming. Acetylene glycol-based surfactants have good affinity (wettability) to ink supply channels and are, accordingly, suitable particularly as cleaning solution.

The acetylene glycol-based surfactant used in the present embodiment may be, but is not limited to, at least one selected from the group consisting of 2,4,7,9-tetramethyl-5-decyne-4,7-diol and alkylene oxide adducts thereof, and 2,4-dimethyl-5-decyne-4-ol and alkylene oxide adducts thereof. The acetylene glycol-based surfactant is commercially available, and examples thereof include, but are not limited to, Olfine 104 series and Olfine E series, such as Olfine E1010 (each a product of Air Products and Chemicals Inc.); and Surfynol 465 and Surfynol 61 (each a product of Nissin Chemical Industry). Acetylene glycol-based surfactants may be used singly or in combination.

Exemplary fluorosurfactants include, but are not limited to, perfluoroalkylsulfonic acid salts, perfluoroalkylcarboxylic acid salts, perfluoroalkylphosphoric acid esters, perfluoroalkylethylene oxide adducts, perfluoroalkylbetaines, and perfluoroalkylamine oxide compounds. Fluorosurfactants are commercially available, and examples thereof include, but are not limited to, S-144 and S-145 (each produced by Asahi Glass); FC-170C, FC-430, and Fluorad-FC4430 (each produced by Sumitomo 3M); FSO, FSO-100, FSN, FSN-100, and FS-300 (each produced by Dupont); and FT-250 and FT-251 (each produced by Neos). Fluorosurfactants may be used singly or in combination.

The silicone surfactant used in the present embodiment may be a polysiloxane compound or a polyether-modified organosiloxane. The silicone surfactant is commercially available, and examples thereof include, but are not limited to, BYK-306, BYK-307, BYK-333, BYK-341, BYK-345, BYK-346, BYK-347, BYK-348, and BYK-349 (each produced by BYK); and KF-351A, KF-352A, KF-353, KF-354L, KF-355A, KF-615A, KF-945, KF-640, KF-642, KF-643, KF-6020, X-22-4515, KF-6011, KF-6012, KF-6015, and KF-6017 (each produced by Shin-Etsu Chemical).

The surfactant content is preferably 0.1% by mass to 5% by mass, more preferably 0.1% by mass to 2% by mass, and still more preferably 0.2% by mass to 1% by mass, relative to the total mass of the ink jet ink composition.

Solvent

Preferably, the ink jet ink composition of the present embodiment further contains a solvent. The solvent may be, but is not limited to, an organic solvent or water.

Water

The ink jet ink composition of the present embodiment may contain water. The water may be pure water or ultrapure water from which ionic impurities have been removed as much as possible. Examples of such water include ion exchanged water, ultrafiltered water, reverse osmosis water, and distilled water. The use of sterile water prepared by, for example, UV irradiation or addition of hydrogen peroxide can reduce the occurrence of mold or bacteria in the ink stored for a long time. The water content in the ink jet ink composition is preferably 50% by mass to 95% by mass, more preferably 60% by mass to 90% by mass, and still more preferably 70% by mass to 80% by mass, relative to the total mass of the ink composition.

Organic Solvent

The ink jet ink composition of the present embodiment may contain an organic solvent.

Examples of the organic solvent include, but are not limited to, glycerin, ethylene glycol, diethylene glycol, triethylene glycol, propylene glycol, dipropylene glycol, 1,3-propanediol, 1,2-butanediol, 1,2-pentanediol, 1,2-hexanediol, 1,4-butanediol, 1,5-pentanediol, 1,6-hexanediol, diethylene glycol mono-n-propyl ether, ethylene glycol mono-isopropyl ether, diethylene glycol mono-isopropyl ether, ethylene glycol mono-n-butyl ether, ethylene glycol mono-t-butyl ether, diethylene glycol mono-n-butyl ether, triethylene glycol monobutyl ether, diethylene glycol mono-t-butyl ether, propylene glycol monomethyl ether, propylene glycol monoethyl ether, propylene glycol mono-t-butyl ether, propylene glycol mono-n-propyl ether, propylene glycol monoisopropyl ether, propylene glycol mono-n-butyl ether, dipropylene glycol mono-n-butyl ether, dipropylene glycol mono-n-propyl ether, dipropylene glycol monoisopropyl ether, diethylene glycol dimethyl ether, diethylene glycol diethyl ether, diethylene glycol dibutyl ether, diethylene glycol ethyl methyl ether, diethylene glycol butyl methyl ether, triethylene glycol dimethyl ether, tetraethylene glycol dimethyl ether, dipropylene glycol dimethyl ether, dipropylene glycol diethyl ether, tripropylene glycol dimethyl ether, methanol, ethanol, n-propyl alcohol, isopropyl alcohol, n-butanol, 2-butanol, tert-butanol, isobutanol, n-pentanol, 2-pentanol, 3-pentanol, tert-pentanol, and other alcohols and glycols; and N,N-dimethylformamide, N,N-dimethylacetamide, 2-pyrrolidone, N-methyl-2-pyrrolidone, 2-oxazolidone, 1,3-dimethyl-2-imidazolidinone, dimethyl sulfoxide, sulfolane, and 1,1,3,3-tetramethyl urea. These organic solvents may be used singly or in combination.

The organic solvent content is preferably 1% by mass to 25% by mass, more preferably 5% by mass to 20% by mass, and still more preferably 10% by mass to 20% by mass, relative to the total mass of the ink jet ink composition.

Other Ingredients

The ink jet ink composition of the present embodiment may further contain, if necessary, one or more of the additives generally used in inks, such as a fungicide, a preservative, an antioxidant, an ultraviolet absorbent, a chelating agent, an oxygen absorbent, a pH adjuster (such as triethanolamine, adipic acid, or tris buffer), and a solubilizing agent. These additional ingredients may be used singly or in combination.

EXAMPLES

The invention will be further described in detail with reference to Examples and Comparative Examples. However, the invention is not limited to the following Examples.

Ingredients of Ink Compositions

The following compounds were major materials used in the ink compositions of the Examples and Comparative Examples.

Coloring Material
  DR 60: C. I. Disperse Red 60
  DY 54: C. I. Disperse Yellow 54
  DB1 359: C. I. Disperse Blue 359
  DR 191: C. I. Disperse Red 191
  DY 163: C. I. Disperse Yellow 163
  DB1 165: C. I. Disperse Blue 165

Dispersant

NS: Sodium naphthalenesulfonate formalin condensate LAVELIN AN-40 (produced by Dai-ichi Kogyo Seiyaku)

Surfactant

BYK 348: Silicone surfactant produced by BYK

Organic Solvent

Gly: Glycerin

TEGMME: Triethylene glycol monomethyl ether

Synthesis of Compound 1

Into the mixture of 1 mol of benzene and 1 mol of benzenesulfonic acid was added 3 mol of sulfuric acid, and the resulting mixture was subjected to a reaction at 150° C. for about 5 hours. Then, calcium carbonate in an amount corresponding to the moles of the added water and sulfuric acid was added for neutralization, followed by rinsing with water. Then, the reaction system was allowed to stand at 0.5 atmosphere and 150° C. for evaporation of unreacted components and excess water to yield the following compound 1:

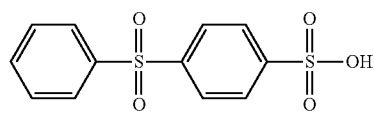

Synthesis of Compound 2

Into 1 mol of naphthalene was added 3 mol of sulfuric acid, and the mixture was subjected to a reaction at 150° C. for about 5 hours. Then, calcium carbonate in an amount corresponding to the moles of the added water and sulfuric acid was added for neutralization, followed by rinsing with water. Then, the reaction system was allowed to stand at 0.5 atmosphere and 150° C. for evaporation of unreacted components and excess water to yield the following compound 2:

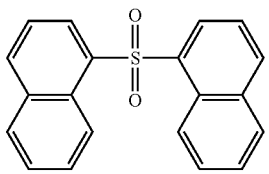 [SMILES: O=S(=O)(c1cccc2ccccc12)c1cccc2ccccc12]

Synthesis of Compound 3

Into the mixture of 1 mol of anthracene and 1 mol of methylanthracene was added 3 mol of sulfuric acid, and the mixture was subjected to a reaction at 150° C. for about 5 hours. Then, calcium carbonate in an amount corresponding to the moles of the added water and sulfuric acid was added for neutralization, followed by rinsing with water. Then, the reaction system was allowed to stand at 0.5 atmosphere and 150° C. for evaporation of unreacted components and excess water to yield the following compound 3:

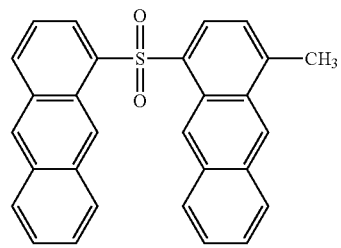 [SMILES: Cc1ccc(S(=O)(=O)c2cccc3cc4ccccc4cc23)c2cc3ccccc3cc12]

Synthesis of Compound 4

Compound 4 represented by the following formula (1') where $R_1$ and $R_2$ are each a $SO_3H$ group was synthesized in the same manner as compound 2, except that 1 mol of naphthalene was replaced with 1 mol of naphthalenesulfonic acid.

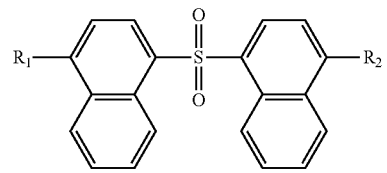

$R_1, R_2 = SO_3H$

Synthesis of Compounds 5A

Compounds 5A represented by the following formula where $R_1$ and $R_2$ are each the corresponding functional group shown in Table 4 or 5 were synthesized in the same manner as compound 2, except that 1 mol of naphthalene, methylnaphthalene, naphthalenesulfonic acid, —$OSO_3H$-substituted naphthalene, naphthalenecarboxylic acid, or naphthol was used as the aromatic compound.

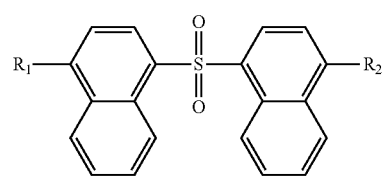

Synthesis of Compound 5B

Compound 5B represented by the following formula where $R_1$ and $R_2$ are each the functional group shown in Table 5 was synthesized in the same manner as compound 2, except that 1 mol of naphthalenesulfonic acid was used as the aromatic compound.

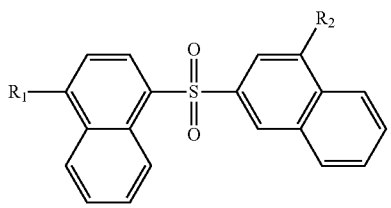

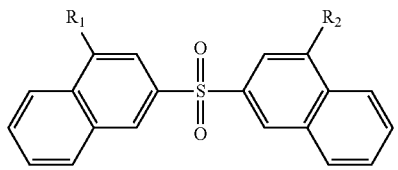

Synthesis of Compound 5C

Compound 5C represented by the following formula where $R_1$ and $R_2$ are each the functional group shown in Table 5 was synthesized in the same manner as compound 2, except that 1 mol of naphthalenesulfonic acid was used as the aromatic compound.

Preparation of Ink Compositions

Ingredients were mixed with the proportions shown in Tables 1 to 4 and fully stirred. Each of the ink compositions was thus prepared. The values in Tables 1 to 4 are on a percent-by-mass basis, and the total content of each composition is 100.0% by mass.

TABLE 1

| | Coloring material (A) | | | Formula (1) compound (B) | | | Dispersant (C) | Surfactant | Organic solvent | | Water | Total | Proportion (A + B)/C | B/A | B/C | Foreign matter rating |
|---|---|---|---|---|---|---|---|---|---|---|---|---|---|---|---|---|
| | DR60 | DY54 | DBI359 | Compound 1 | Compound 2 | Compound 3 | NS | BYK348 | Gly | TEGMME | | | | | | |
| Example 1 | 3 | — | — | 3 | — | — | 6 | 0.5 | 10 | 3 | Balance | 100 | 1.00 | 1.00 | 0.500 | A |
| Example 2 | 3 | — | — | — | 3 | — | 6 | 0.5 | 10 | 3 | Balance | 100 | 1.00 | 1.00 | 0.500 | A |
| Example 3 | 3 | — | — | — | — | 3 | 6 | 0.5 | 10 | 3 | Balance | 100 | 1.00 | 1.00 | 0.500 | A |
| Example 4 | 1 | 0.5 | 1 | 2.5 | — | — | 5 | 0.5 | 10 | 3 | Balance | 100 | 1.00 | 1.00 | 0.500 | A |
| Example 5 | 1 | 0.5 | 1 | — | 2.5 | — | 5 | 0.5 | 10 | 3 | Balance | 100 | 1.00 | 1.00 | 0.500 | A |
| Example 6 | 1 | 0.5 | 1 | — | — | 2.5 | 5 | 0.5 | 10 | 3 | Balance | 100 | 1.00 | 1.00 | 0.500 | A |
| Comparative Example 1 | 3 | — | — | — | — | — | 6 | 0.5 | 10 | 3 | Balance | 100 | — | 0 | 0 | E |
| Comparative Example 2 | 1 | 0.5 | 1 | — | — | — | 5 | 0.5 | 10 | 3 | Balance | 100 | — | 0 | 0 | E |

TABLE 2

| | Coloring material (A) | | | Formula (1) compound (B) | | | Dispersant (C) | Surfactant | Organic solvent | | Water | Total | Proportion (A + B)/C | B/A | B/C | Foreign matter rating |
|---|---|---|---|---|---|---|---|---|---|---|---|---|---|---|---|---|
| | DR191 | DY163 | DBI165 | Compound 1 | Compound 2 | Compound 3 | NS | BYK348 | Gly | TEGMME | | | | | | |
| Example 7 | 3 | — | — | 3 | — | — | 6 | 0.5 | 10 | 3 | Balance | 100 | 1.00 | 1.00 | 0.500 | A |
| Example 8 | 3 | — | — | — | 3 | — | 6 | 0.5 | 10 | 3 | Balance | 100 | 1.00 | 1.00 | 0.500 | A |
| Example 9 | 3 | — | — | — | — | 3 | 6 | 0.5 | 10 | 3 | Balance | 100 | 1.00 | 1.00 | 0.500 | A |
| Example 10 | 1 | 0.5 | 1 | 2.5 | — | — | 5 | 0.5 | 10 | 3 | Balance | 100 | 1.00 | 1.00 | 0.500 | A |
| Example 11 | 1 | 0.5 | 1 | — | 2.5 | — | 5 | 0.5 | 10 | 3 | Balance | 100 | 1.00 | 1.00 | 0.500 | A |
| Example 12 | 1 | 0.5 | 1 | — | — | 2.5 | 5 | 0.5 | 10 | 3 | Balance | 100 | 1.00 | 1.00 | 0.500 | A |
| Comparative Example 3 | 3 | — | — | — | — | — | 6 | 0.5 | 10 | 3 | Balance | 100 | — | 0 | 0 | E |
| Comparative Example 4 | 1 | 0.5 | 1 | — | — | — | 5 | 0.5 | 10 | 3 | Balance | 100 | — | 0 | 0 | E |

TABLE 3

| | Coloring material (A) | Formula (1) compound (B) Compound 4 | Dispersant (C) | Surfactant | Organic solvent | | Water | Total | Proportion | | | Foreign matter rating |
|---|---|---|---|---|---|---|---|---|---|---|---|---|
| | DR60 | (R$_1$=R$_2$=SO$_3$H) | NS | BYK348 | Gly | TEGMME | | | (A + B)/C | B/A | B/C | |
| Example 13 | 0.1 | 0.1 | 0.1 | 0.5 | 10 | 3 | Balance | 100 | 2.00 | 1.00 | 1.000 | A |
| Example 14 | 0.1 | 1 | 1 | 0.5 | 10 | 3 | Balance | 100 | 1.10 | 10.00 | 1.000 | A |
| Example 15 | 0.1 | 10 | 10 | 0.5 | 10 | 3 | Balance | 100 | 1.01 | 100.00 | 1.000 | A |
| Example 16 | 0.1 | 15 | 15 | 0.5 | 10 | 3 | Balance | 100 | 1.01 | 150.00 | 1.000 | A |
| Example 17 | 0.1 | 0.1 | 5 | 0.5 | 10 | 3 | Balance | 100 | 0.04 | 1.00 | 0.020 | C |
| Example 18 | 0.1 | 1 | 5 | 0.5 | 10 | 3 | Balance | 100 | 0.22 | 10.00 | 0.200 | C |
| Example 19 | 0.1 | 10 | 5 | 0.5 | 10 | 3 | Balance | 100 | 2.02 | 100.00 | 2.000 | A |
| Example 20 | 0.1 | 15 | 5 | 0.5 | 10 | 3 | Balance | 100 | 3.02 | 150.00 | 3.000 | B |
| Example 21 | 1 | 0.1 | 0.1 | 0.5 | 10 | 3 | Balance | 100 | 11.00 | 0.10 | 1.000 | C |
| Example 22 | 1 | 1 | 1 | 0.5 | 10 | 3 | Balance | 100 | 2.00 | 1.00 | 1.000 | A |
| Example 23 | 1 | 10 | 10 | 0.5 | 10 | 3 | Balance | 100 | 1.10 | 10.00 | 1.000 | A |
| Example 24 | 1 | 15 | 15 | 0.5 | 10 | 3 | Balance | 100 | 1.07 | 15.00 | 1.000 | A |
| Example 25 | 1 | 0.1 | 5 | 0.5 | 10 | 3 | Balance | 100 | 0.22 | 0.10 | 0.020 | C |
| Example 26 | 1 | 1 | 5 | 0.5 | 10 | 3 | Balance | 100 | 0.40 | 1.00 | 0.200 | B |
| Example 27 | 1 | 10 | 5 | 0.5 | 10 | 3 | Balance | 100 | 2.20 | 10.00 | 2.000 | A |
| Example 28 | 1 | 15 | 5 | 0.5 | 10 | 3 | Balance | 100 | 3.20 | 15.00 | 3.000 | B |
| Example 29 | 1 | 10 | 1 | 0.5 | 10 | 3 | Balance | 100 | 11.00 | 10.00 | 10.000 | B |
| Example 30 | 10 | 0.1 | 0.1 | 0.5 | 10 | 3 | Balance | 100 | 101.00 | 0.01 | 1.000 | C |
| Example 31 | 10 | 1 | 1 | 0.5 | 10 | 3 | Balance | 100 | 11.00 | 0.10 | 1.000 | C |
| Example 32 | 10 | 10 | 10 | 0.5 | 10 | 3 | Balance | 100 | 2.00 | 1.00 | 1.000 | A |
| Example 33 | 10 | 15 | 15 | 0.5 | 10 | 3 | Balance | 100 | 1.67 | 1.50 | 1.000 | B |
| Example 34 | 10 | 0.1 | 5 | 0.5 | 10 | 3 | Balance | 100 | 2.02 | 0.01 | 0.020 | C |
| Example 35 | 10 | 1 | 5 | 0.5 | 10 | 3 | Balance | 100 | 2.20 | 0.10 | 0.200 | C |
| Example 36 | 10 | 10 | 5 | 0.5 | 10 | 3 | Balance | 100 | 4.00 | 1.00 | 2.000 | C |
| Example 37 | 10 | 15 | 5 | 0.5 | 10 | 3 | Balance | 100 | 5.00 | 1.50 | 3.000 | C |
| Example 38 | 10 | 10 | 1 | 0.5 | 10 | 3 | Balance | 100 | 20.00 | 1.00 | 10.000 | C |
| Example 39 | 10 | 1 | 10 | 0.5 | 10 | 3 | Balance | 100 | 1.10 | 0.10 | 0.100 | A |
| Example 40 | 10 | 10 | 20 | 0.5 | 10 | 3 | Balance | 100 | 1.00 | 1.00 | 0.500 | A |
| Comparative Example 5 | 0.1 | — | 15 | 0.5 | 10 | 3 | Balance | 100 | — | — | — | E |
| Comparative Example 6 | 1 | — | 15 | 0.5 | 10 | 3 | Balance | 100 | — | — | — | E |

TABLE 4

| | | Coloring material (A) | Formula (1) compound (B) Compound 5A | Dispersant (C) | Surfactant | Organic solvent | | Water | Total | Proportion | | | Foreign matter rating |
|---|---|---|---|---|---|---|---|---|---|---|---|---|---|
| | | DR60 | | NS | BYK348 | Gly | TEGMME | | | (A + B)/C | B/A | B/C | |
| Example 41 | R$_1$=R$_2$=H | 5 | 5 | 10 | 0.5 | 10 | 3 | Balance | 100 | 1.00 | 1.00 | 0.500 | A |
| Example 42 | | 5 | 10 | 10 | 0.5 | 10 | 3 | Balance | 100 | 1.50 | 2.00 | 1.000 | B |
| Example 43 | | 5 | 20 | 10 | 0.5 | 10 | 3 | Balance | 100 | 2.50 | 4.00 | 2.000 | C |
| Example 44 | R$_1$=R$_2$=CH$_3$ | 5 | 5 | 10 | 0.5 | 10 | 3 | Balance | 100 | 1.00 | 1.00 | 0.500 | A |
| Example 45 | | 5 | 10 | 10 | 0.5 | 10 | 3 | Balance | 100 | 1.50 | 2.00 | 1.000 | B |
| Example 46 | | 5 | 20 | 10 | 0.5 | 10 | 3 | Balance | 100 | 2.50 | 4.00 | 2.000 | C |
| Example 47 | R$_1$=R$_2$=SO$_3$H | 5 | 5 | 10 | 0.5 | 10 | 3 | Balance | 100 | 1.00 | 1.00 | 0.500 | A |
| Example 48 | | 5 | 10 | 10 | 0.5 | 10 | 3 | Balance | 100 | 1.50 | 2.00 | 1.000 | A |
| Example 49 | | 5 | 20 | 10 | 0.5 | 10 | 3 | Balance | 100 | 2.50 | 4.00 | 2.000 | B |
| Example 50 | R$_1$=R$_2$=OSO$_3$H | 5 | 5 | 10 | 0.5 | 10 | 3 | Balance | 100 | 1.00 | 1.00 | 0.500 | A |
| Example 51 | | 5 | 10 | 10 | 0.5 | 10 | 3 | Balance | 100 | 1.50 | 2.00 | 1.000 | A |
| Example 52 | | 5 | 20 | 10 | 0.5 | 10 | 3 | Balance | 100 | 2.50 | 4.00 | 2.000 | B |
| Example 53 | R$_1$=R$_2$=COOH | 5 | 5 | 10 | 0.5 | 10 | 3 | Balance | 100 | 1.00 | 1.00 | 0.500 | A |
| Example 54 | | 5 | 10 | 10 | 0.5 | 10 | 3 | Balance | 100 | 1.50 | 2.00 | 1.000 | A |
| Example 55 | | 5 | 20 | 10 | 0.5 | 10 | 3 | Balance | 100 | 2.50 | 4.00 | 2.000 | B |
| Example 56 | R$_1$=R$_2$=OH | 5 | 5 | 10 | 0.5 | 10 | 3 | Balance | 100 | 1.00 | 1.00 | 0.500 | A |
| Example 57 | | 5 | 10 | 10 | 0.5 | 10 | 3 | Balance | 100 | 1.50 | 2.00 | 1.000 | A |
| Example 58 | | 5 | 20 | 10 | 0.5 | 10 | 3 | Balance | 100 | 2.50 | 4.00 | 2.000 | C |

TABLE 5

| | | Coloring material (A) DR60 | Formula (1) compound (B) | | | Dispersant (C) NS | Surfactant BYK348 | Foreign matter rating | Organic solvent | | Water | Total | Proportion | | | Foreign matter rating |
|---|---|---|---|---|---|---|---|---|---|---|---|---|---|---|---|---|
| | | | Compound 5A | Compound 5B | Compound 5C | | | | Gly | TEGMME | | | (A + B)/C | B/A | B/C | |
| Example 59 | $R_1=R_2=SO_3H$ | 5 | 3 | 3 | 3 | 10 | 0.5 | A | 10 | 3 | Balance | 100 | 1.40 | 1.80 | 0.900 | A |
| Example 60 | | 5 | 5 | 3 | 1 | 10 | 0.5 | A | 10 | 3 | Balance | 100 | 1.40 | 1.80 | 0.900 | A |
| Example 61 | | 5 | 3 | 1 | 5 | 10 | 0.5 | A | 10 | 3 | Balance | 100 | 1.40 | 1.80 | 0.900 | A |
| Example 62 | | 5 | 1 | 5 | 3 | 10 | 0.5 | A | 10 | 3 | Balance | 101 | 1.40 | 1.80 | 0.900 | A |
| Example 63 | | 5 | 5 | 4 | — | 10 | 0.5 | A | 10 | 3 | Balance | 102 | 1.40 | 1.80 | 0.900 | A |
| Example 64 | | 5 | 4 | — | 5 | 10 | 0.5 | A | 10 | 3 | Balance | 102 | 1.40 | 1.80 | 0.900 | A |
| Example 65 | | 5 | — | 5 | 4 | 10 | 0.5 | A | 10 | 3 | Balance | 102 | 1.40 | 1.80 | 0.900 | A |

Checking for Foreign Matter

The ink compositions, each of 30 mL in volume, were enclosed in respective test ink packs so as to avoid entrance of air, and the test ink packs were allowed to stand at 60° C. for 5 days. Then, 10 mL each of the ink compositions was filtered through a metal mesh filter (pore size: 10 μm), and the number of pieces of foreign matter on the metal mesh filter per 1 mm square was counted. The resulting number of pieces of foreign matter was rated according to the following criteria:

A: The number of pieces of crystalline foreign matter was 0 per 1 mm square.

B: The number of pieces of crystalline foreign matter was 1 to 5 per 1 mm square.

C: The number of pieces of crystalline foreign matter was 6 to 25 per 1 mm square.

D: The number of pieces of crystalline foreign matter was 26 to 50 per 1 mm square.

E: The number of pieces of crystalline foreign matter was 51 or more per 1 mm square.

The entire disclosure of Japanese Patent Application Nos. 2016-194422, filed Sep. 30, 2016 and 2017-112297, filed Jun. 7, 2017 are expressly incorporated by reference herein.

What is claimed is:

1. An ink jet ink composition comprising:

a disperse dye;

a formalin condensate of an aromatic sulfonic acid compound; and a compound represented by the following formula (1):

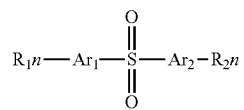

(1)

wherein $Ar_1$ and $Ar_2$ each independently represent an aryl group, $R_1$ and $R_2$ each independently represent a chemical species selected from the group consisting of hydrogen, alkyl groups having a carbon number of 1 to 3, a sulfo group, —O—$SO_3H$, a carboxy group, and a hydroxy group, and n's each independently represent an integer of 0 to 5.

2. The ink jet ink composition according to claim 1, wherein a proportion of the compound represented by formula (1) relative to 1 part by mass of the disperse dye is 0.01 part by mass to 150 parts by mass.

3. The ink jet ink composition according to claim 1, further comprising a dispersant.

4. The ink jet ink composition according to claim 1, wherein a proportion of a total mass of the disperse dye and the compound represented by formula (1) is in a range of 0.24 to 4.0 relative to a mass of a dispersant.

5. The ink jet ink composition according to claim 1, wherein a proportion of the compound represented by formula (1) relative to 1 part by mass of a dispersant is 0.001 part by mass to 1000 parts by mass.

6. The ink jet ink composition according to claim 1, wherein a molecule of the disperse dye has a condensed ring structure.

* * * * *